Figure 1:
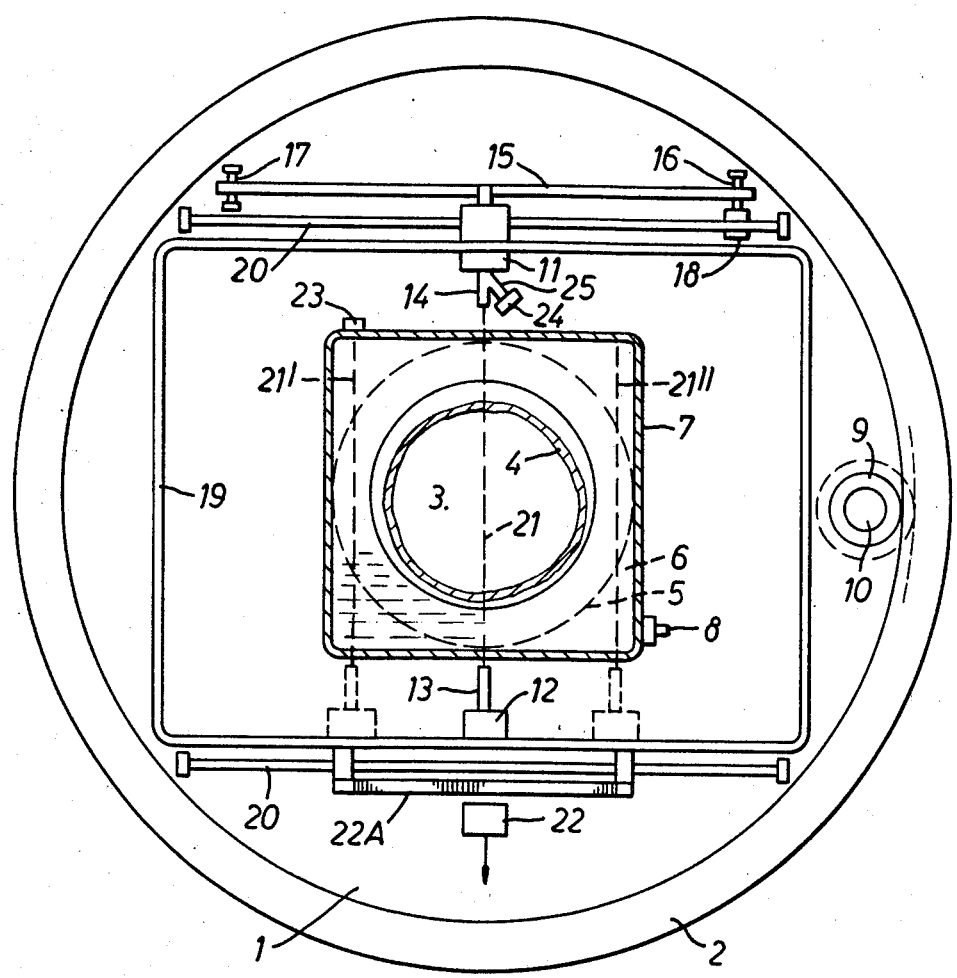

United States Patent [19]

Hounsfield

[11] 4,052,619
[45] Oct. 4, 1977

[54] METHOD AND APPARATUS FOR MEASURING AND ANALYZING RADIATION TRANSMITTED AT PLURAL ANGLES

[75] Inventor: Godfrey Newbold Hounsfield, Newark, England

[73] Assignee: EMI Limited, Hayes, England

[21] Appl. No.: 547,337

[22] Filed: Feb. 5, 1975

[30] Foreign Application Priority Data

Feb. 15, 1974 United Kingdom ............... 6884/74

[51] Int. Cl.² .................. G01T 1/20; G01N 13/04
[52] U.S. Cl. ....................... 250/363 S; 250/445 T
[58] Field of Search ............ 250/363 S, 362, 445 T, 250/503

[56] References Cited

U.S. PATENT DOCUMENTS

| | | | |
|---|---|---|---|
| 3,432,657 | 3/1969 | Slavin | 250/359 |
| 3,499,146 | 3/1970 | Richards | 250/445 T |
| 3,778,614 | 12/1973 | Hounsfield | 250/363 |
| 3,780,290 | 12/1973 | Hoffer | 250/363 S |
| 3,784,820 | 1/1974 | Miraldi | 250/362 |
| 3,808,440 | 4/1974 | Petit-Clerc | 250/363 S |
| 3,862,425 | 1/1975 | Myers | 250/363 S |
| 3,924,129 | 12/1975 | Le May | 250/362 |

*Primary Examiner*—Alfred E. Smith
*Assistant Examiner*—David K. Moore
*Attorney, Agent, or Firm*—Fleit & Jacobson

[57] ABSTRACT

In an apparatus for examining a body by means of penetrating radiation a source of the radiation and a detector are arranged to orbit about the body. Data obtained from the detector are used to provide a representation of the distribution of absorption in part of the body. To reduce patient movement artefacts in the reconstructed image some of the data are obtained for substantially the same radiation paths through the body, but at different times, and are combined after weighting by complementary factors.

6 Claims, 5 Drawing Figures

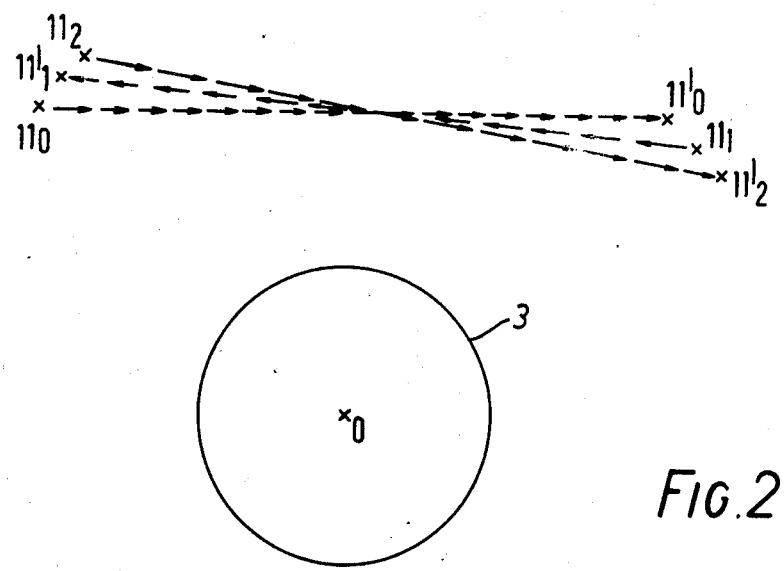
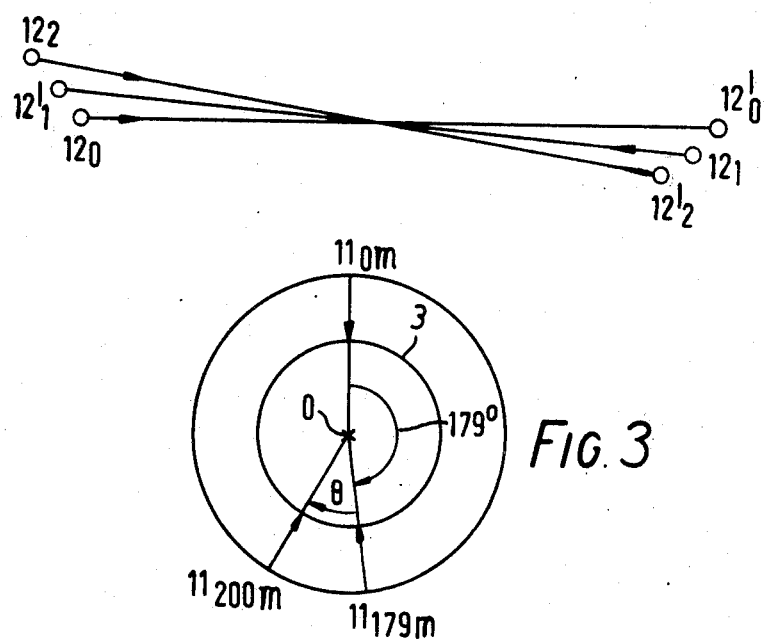
FIG.2
FIG.3
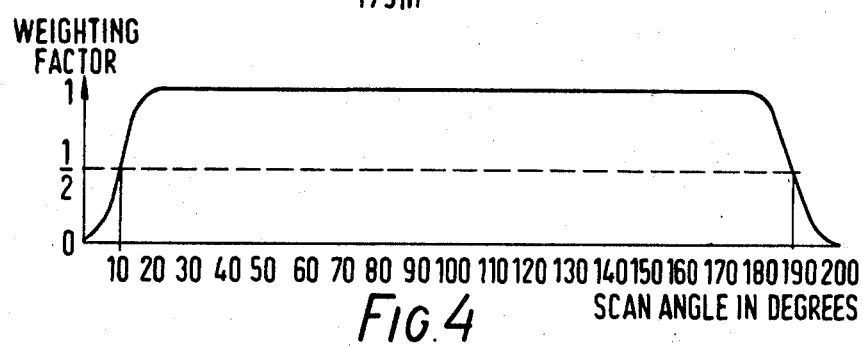
FIG.4

METHOD AND APPARATUS FOR MEASURING AND ANALYZING RADIATION TRANSMITTED AT PLURAL ANGLES

The present invention relates to radiological apparatus, and it relates especially, though not exclusively to such apparatus of the general nature disclosed in U.S. Pat. No. 3,778,614.

Apparatus of the kind described in the aforementioned patent includes a source of penetrating radiation, such as X- or γ- radiation, and detector means responsive to said radiation, the source and detector means being scanned, in a plane, relative to a body under examination in such a way that the detector means produces output signals indicative of the absorption suffered by the radiation as it traverses many different paths through the body in the plane of the scan.

The scanning of the source and the detector means relative to the body involves, inter alia, rotating the two components around the body through an angle of, for example, 180° or 360°, and consequently an appreciable time lapse occurs between the scanning at the first angle and the scanning at the last angle of the rotational sequence, the consequence being that motion of (say) fluid within or around the body in the region of examination can give considerable variations in the absorption suffered by the radiation as between the first and last scanning angles, which relate to closely adjacent portions of the body.

The phenomenon described in the last preceding paragraph can give rise to undesirable streaking effects when a visual representation of the absorption coefficients of small elements of the body, in the plane of examination, is produced. These streaking effects are most pronounced at the angle which corresponds to the "abutment" of the first and last scans of the rotational sequence. It is an object of this invention to provide radiological apparatus in which the above-mentioned streaking effects are reduced (or eliminated).

According to one aspect of the invention there is provided an apparatus for examining a body by means of penetrating radiation such as X- or γ-radiation including source means arranged to irradiate a region of the body, detector means responsive to said radiation and disposed to receive said radiation after passage through the body to provide output signals for processing to construct a representation of the distribution of the absorption of the radiation in parts of the body, means for rotating the source and detector means around the body to irradiate the body from a plurality of directions and processing means arranged to multiply some of the output signals derived from said detector means relating to substantially the same path through the body, but obtained at different times in said rotation, by complementary factors and thereafter to combine said signals.

According to a further aspect of the invention there is provided an apparatus for examining a body by means of penetrating radiation such as X- or γ-radiation including source means arranged to irradiate a region of the body, detector means responsive to said radiation and disposed to receive said radiation after passage through the body to provide output signals for processing to construct a representation of the distribution of the absorption of the radiation in parts of the body, means for rotating the source and detector means around the body to irradiate the body from a plurality of directions and processing means arranged to combine some of the output signals derived from the detector means relating to substantially the same path through the body, but obtained at different times in said rotation, in accordance with a predetermined amplitude ratio which varies throughout a predetermined angular range of said rotation.

Figure 5:
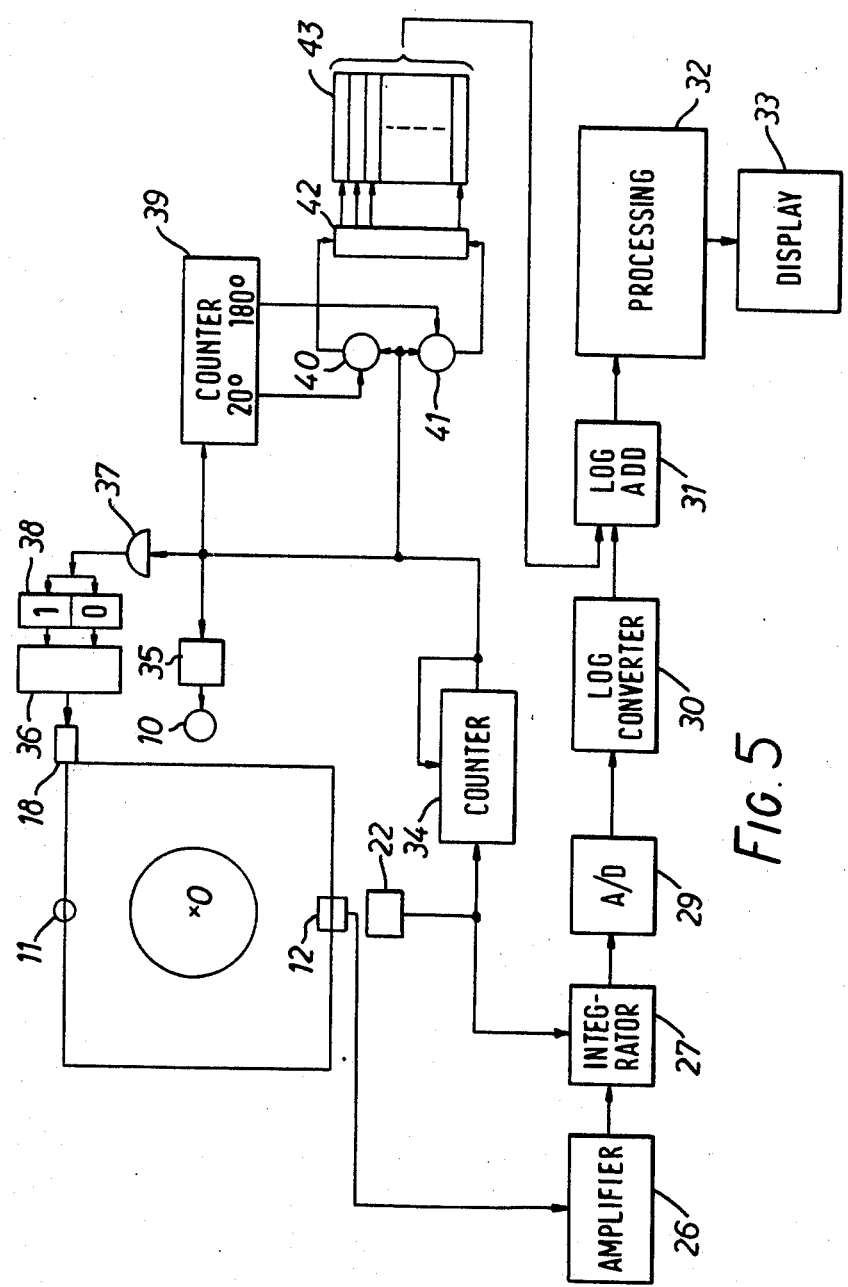

In order that the invention may be clearly understood and readily carried into effect, one embodiment thereof will now be described, by way of example only, with reference to the accompanying drawings of which:

FIG. 1 shows an apparatus suitable for use with the invention,

FIG. 2 shows, in schematic manner the motions used for scanning the radiation relative to a body to be examined in the apparatus of FIG. 1, FIG. 3 shows, in similar view to FIG. 2, an overlap scanning technique, FIG. 4 shows a graph of weighting factor versus angle of scan, the weighting factor being unity for angles at which no overlap occurs, and FIG. 5 shows in block diagrammatic form a suitable circuit arrangement for use with the invention.

Referring to the drawings, FIG. 1 shows a form of apparatus, for the purpose referred to hereinbefore, which is adapted to examination of the head, although it is stressed that the invention is not limited in its application to radiological apparatus using this scanning technique. The apparatus comprises a rotary member 1 which is rotatable inside a fixed casing 2 forming part of the main frame of the apparatus. The rotary member 1 has a central aperture 3 in which the head of the patient to be examined can be inserted. The central aperture is closed in a water-tight manner by a pouched cover 4 of flexible material which is secured to a sealing flange 5. This flange is held in sealing, but rotatable, relationship with the remote face of the member 1. The pouch is shown in section in FIG. 1. The head of the patient is introduced through the aperture 3 to the pouch of the cover 1, and an additional head rest, which is not shown, may be provided to support the head in the pouch. A suitable support is provided for the patient during the examination. When the head is inserted through the aperture 3 into the pouch 4 it projects into a water reservoir 6 having side walls 7, the pouch separating the head from the water. The reservoir is closed at the front by a member 1 and cover 4, at the side by the walls 7 which are made of plastic, and at the rear by a base wall not shown. The walls of the reservoir, other than the cover 4 are carried by or formed by the rotary member 1, so that the reservoir rotates with the member 1 around the head. Instead of surrounding the head with water it may be suitably enclosed in any conveient material which has an X-ray absorption similar to body tissue. The walls 7 and the base wall rotate with the member 1, whereas the cover 4 with its flange 5 remains stationary, the flange being secured to the frame of the apparatus. A pipe 8 is connected to a pump for feeding water to and from the reservoir and after the patient's head has been inserted in the pouch, water is pumped into the reservoir 6 so as to expel the air from between the pouch and the patient's head.

A toothed gear wheel 9, driven by a motor 10 is provided for driving the rotatable member so as to produce orbital scanning of the member 1 about its axis, which is also the axis of the aperture 3. The gear wheel 9 engages teeth formed around the inner periphery of the casing 2. The rotatable member carries a source 11 of penetrating radiation, an X-ray tube in this example and facing the source 11, on the other side of the aperture 3 there is provided an X-ray detector 12. The detector 12, which comprises a scintillator crystal and a photomultiplier has a collimator 13. The source of the radiation 11 is arranged to be an effective point source and it has a collimator 14 confining the radiation, with collimator 13 to a single narrow beam 21 lying in a plane section normal to the axis of rotary member 1. The plane lies within reservoir 6.

The source 11 is secured to a toothed belt 15 driven by a toothed drive shaft 16 journalled in the rotatable member 1, the belt being extended between the shaft 16 and the second shaft 17 also journalled in member 1. The shaft 16 is driven by a reversible motor 18, the controls of which are interlocked with those of motor 10. A counter weight, not shown, is provided secured to the other rim of the belt so as to move reciprocally with the source. In operation, the source 11 and the collimator 14 are caused by the motor 18 to execute to and fro lateral scanning movements in the aforementioned plane normal to the axis of member 1. The detector 12 with its collimator 13 are coupled to the source 11 by the yoke 19 so that they execute the same lateral scanning movements. Guides 20 are provided to support the source and the yoke during the lateral scanning. The extremities of the scan are shown by dotted lines 21' and 21''.

A lead block 23 provides substantially complete absorption of the X-radiation for position 21' of the X-rays and enables a determination of afterglow in the detector. A second reference reading at position 21'' is entirely through a standard attenuator, the water in reservoir 6, allowing a calibrating reading.

A reference detector 24 is mounted close to the X-ray source 11 so that it receives radiation directly from the source, via a collimator 25, tp monitor the intensity of the X-rays.

The apparatus so far described is generally similar to that described in U.S. Pat. No. 3,924,129, but, as will be explained with reference to the following figures the scanning of the apparatus is adapted in accordance with the invention to reduce movement artefacts in the reconstructed images.

FIG. 2 shows, in simplified form, the scanning motion obtained in the apparatus of FIG. 1. The centre of rotation is shown at the axis O.

The scanning operation commences, with the source and detector means disposed in the positions shown as $11_o$ and $12_o$ respectively, and they are traversed by motor 18 linearly in one sense towards $11_o'$ and $12_o'$ respectively. When the source and the detector means have reached their respective positions $11_o'$ and $12_o'$ the scanning frame is rotated clockwise through a small angle (e.g. 1°) so that the source and the detector means are moved to the positions $11_1$ and $12_1$ respectively. The angular motion is shown on an exaggerated scale in FIG. 2 for clarity of the drawing. The source and the detector means are then linearly traversed in the reverse sense, relative to the aperture 3, towards the point $11_1'$ and $12_1'$ respectively and when these positions are reached, the scanning frame is rotated through a further step of 1° in the clockwise direction, thus moving the source and detector means to the positions $11_2$ and $12_2$ respectively, when another linear traverse occurs to take the source and detector means to $11_2'$ and $12_2'$ respectively. This sequence of alternating linear traverses and rotational steps is continued until the scanning frame has rotated through 179° (in this example). After this, further rotation of the scanning frame irradiates the body from angles from which the body has already been irradiated, the only difference being that the radiation passes through the body in the reverse direction in the second case. FIG. 3 shows the aperture 3 on a reduced scale and shows some salient positions of the source 11 around the aperture, the source 11 being indicated at the mid point of its linear traverse in each case, as indicated by the subscript $m$. Position $11_{om}$ corresponds to the source 11 at the mid point of its traverse between positions $11_o$ and $11_o'$. Assuming that the scanning frame is rotated in steps of 1°, the mid point of the last scan occurs at $11_{179m}$. As mentioned previously, however, an appreciable time lag occurs between the scans 0 and 179. If no changes have occurred between the two scans, the output signals provided by the detector means should be substantially the same in each case, since it will be appreciated that a beam of radiation from $11_{om}$ passing through 0 follows an extremely close path (through the body) to that followed by a beam of radiation from $11_{179m}$ passing through 0. In these circumstances, no streaking occurs. However, if a change has occurred in the plane of investigation, for example a shift of sinus fluid within the body or of an air bubble entrapped in the region immediately surrounding the body, then the two close paths (followed by radiation from the source at $11_{om}$ and $11_{179m}$) can exhibit markedly different absorptions to the radiation. In these circumstances the aforementioned streaking would arise in the reconstructed image but for the provision of the present invention.

In accordance with this example of the invention, the alternating transverse and rotational scans are continued for a further angle $\theta$ beyond the 179° position. Typically $\theta$ can equal 21° so that the total angle of scan is 200°. The information derived from the detector 12 in the angular region in which no overlap occurs (i.e. the region from 20° to 179°) is allocated a weighting factor of unity. However the information derived from the detector 12 in the angular region in which overlap occurs is weighted in accordance with a law of the kind shown in FIG. 4 whence it can be seen that the information derived when the source 11 assumes positions $11_0$ to $11_{20}$ is multiplied by a weighting factor which varies between 0 and 1 while the information derived when the source 11 assumes positions $11_{180}$ to $11_{200}$ is multiplied by a weighting factor which varies between 1 and 0 such that when the information derived from corresponding beams (i.e. with the source at positions $11_0$ and $11_{180}$; $11_1$ and $11_{181}$; $11_2$ and $11_{182}$ etc. up to $11_{20}$ and $11_{200}$) are added, their weighting factors always total unity. By this means, if any changes have occurred the streaking is diffused and is less noticeable, whereas if no changes have occurred then no degradation is introduced.

It will be evident that the scanning frame could be rotated through a greater angle than 179°, for example 359° or more and that the angular range $\theta$ need not be 21°, it may be any convenient range.

FIG. 5 illustrates part of the control and processing arrangement for the scanning apparatus illustrated in FIG. 1. The scanning apparatus is represented by the source 11, detector 12, motors 10 and 18 and photocell device 22. Assuming that the scanning has commenced with the source in position $11_o$ and the detector correspondingly in position $12_o$ then during the following lateral scan to $11_o'$ and $12_o'$ the graticule 22a (FIG. 1)

will pass before photocell device 22. The device 22 will thus deliver successive pulses to a counter 34 and to an integrator 27. The output current from the detector 12 is fed to the integrator via an amplifier 26. Integrator 27, which may be of the well known Miller type, is read and reset at intervals in response to each pulse from 22. The intervals are determined by the pitch of lines on the graticule. Thus the output current is formed into discrete data signals each representing a beam path defined by the length of scan between each pulse. The data signals are converted to digital form in an analogue-digital converter 29 and converted to logarithmic form, as required for the processing referred to hereinafter in a converter 30 before being passed to a logarithmic adder 31 as will be explained hereinafter. From adder 31 they are fed to a processing unit 32 where they are used to form a distribution of absorption coefficients by a method such as the method described in the said U.S. Pat. No. 3,778,614 or that described in U.S. Pat. No. 3,924,129. This distribution is displayed in a display unit 33. Adder 31 is arranged to multiply the data signals by the appropriate weighting factor as shown in FIG. 4, the weighting factor being drawn from a store 43 in a manner to be explained and are added logarithmically to obtain the desired multiplication. As has been mentioned, the data signals for the first 20° of scan are added to those for the last 20° of scan. Since this is a known factor for the geometry of the apparatus, the input store of processing unit 32 will have the relevant data stored in known locations and can readily effect the addition. Alternatively an intermediate store responding to signals from counter 31 can be provided. It will be appreciated that since the signals are in logarithmic form at this stage straightforward addition would produce multiplication. Appropriate steps must therefore be taken. Alternatively the log conversion provided by counter 30 may be postponed until after the multiplication remembering that unit 31 must be a multiplier.

The control of the apparatus is effected in response to the signals from unit 22. These are counted in the counter 34 which is arranged to provide an output pulse after a predetermined number of such pulses, to indicate the end of the lateral scan. The output pulse is provided to unit 35 controlling motor 10 to initiate the predetermined orbital movement. The pulse is also provided to unit 36 controlling motor 18, after an appropriate delay in delay unit 37 to ensure that the orbital movement is complete, to initiate the next lateral scan. The input to unit 36 is to either 'left scan' or 'right scan' inputs via a flip-flop 38 so that alternate lateral scans are in opposite directions. The pulse from counter 34 is also applied to a resetting input thereon to commence the count for the next lateral scan at zero.

The pulses from 34 indicating an orbital movement are applied also to a counter 39 which gives output pulses for each such movement at one terminal for the first 20° of scan and at another for the last 20° of scan (from 180° on) to enabling inputs of respective gates 40 and 41. These gates, when enabled, apply the pulses from 34 to a shift register 42 in one or other direction as indicated. Shift register 42 has sufficient locations for the overlapping part of the scan and has a control signal moved up or down in step with the orbital movements. The control signal is used to control store 43 such that the required weighting factor is withdrawn from a location of store 43 corresponding to the position of the control signal in register 42 at any time. The weighting factors in store 43 are held in logarithmic form so that by adding in unit 31 with the detector output signals, also in logarithmic form, multiplication is obtained. Since the data for 0° and 200° are to be multiplied by a weighting factor of zero they may be omitted by appropriate gating of the circuit. This is desirable since the log of the weighting factor zero would properly be one.

It will be understood that other circuits may be devised to apply the principles of the invention and that many of the functions described maybe performed by the digital computer referred to hereinbefore.

In the example of the invention described above the invention is used in a medical radiology machine of the type sometimes referred to as a CAT scanner, in which radiation travels along a substantially planar slice through the patient. The X-radiation source orbits around the patient so as to send radiation along a number of directions which are at different angles to each other in the slice. The intensity of the radiation emerging from the slice is measured along each of a number of pencil-thin beam paths such that any point in the slice is traversed by a great number of such beam paths. The resulting measurements are processed, for example, as described in U.S. Pat. Nos. 3,778,614 and 3,924,129 to generate a picture in which each point has a brightness corresponding to the X-radiation response characteristics of the correspondingly positioned point in the slice. The picture is similar to what would be seen if the patient were cut in two along the slice and one looked at the resulting cross section through the body.

While orbiting the source over half a revolution is sufficient, using the type of scanning described herein, to derive the required picture, the picture is sometimes degraded when the radiation detected along the substantially identical or similar beam paths at the start and end of the orbiting is not substantially identical, as it should be, due to motion of the patient or within the patient that has occurred between the start and the end of the orbiting. The resulting degrading of the picture sometimes appears as streaks or lines across the picture. In order to avoid or reduce such degrading of the picture, one aspect of this invention relates to extending the orbiting motion to include some angle, say 20°, in addition to the necessary half revolution, and combining the detected radiation for the first and the last portions of the orbiting so as to reduce or at least distribute over a large portion of the picture any errors which are due to motion of or within the patient that has occurred during the orbiting. In the specific embodiment described above, during the last portion of the orbit radiation is detected along beam paths which are along the same lines as beam paths during the first portion of the orbit but are at opposite directions. Pairs of measurement signals for beam paths at opposite directions form a combined measurement signal to which each measurement signal contributes an amount determined by its angular position within the orbit such that the combined signal has a magnitude corresponding to that detected along a single beam path and can be used later in processing together with the measurement signals for beam paths from the central portion of the orbit.

What I claim is:

1. An apparatus for examining a body by means of penetrating radiation such as X- or γ-radiation including source means arranged to irradiate a cross-sectional slice of the body, detector means responsive to said radiation and disposed to receive said radiation after passage through the body along a plurality of substantially linear paths and to provide corresponding output signals for processing to construct a representation of the distribution of the absorption of the radiation over said slice, means for rotating the source and detector means around the body causing said source means to irradiate the slice from a plurality of directions and said detector means to provide further output signals, relating to further substantially linear paths, and processing means arranged to multiply some of the output signals derived from said detector means and relating to substantially the same path through the body, but obtained at different times during said rotation, by complementary factors which vary with the extent of said rotation and thereafter to combine said signals.

2. An apparatus for examining a body by means of penetrating radiation such as X- or γ-radiation including source means arranged to irradiate a cross-sectional slice of the body, detector means responsive to said radiation and disposed to receive said radiation after passage through the body along a plurality of substantially linear paths and to provide corresponding output signals for processing to construct a representation of the distribution of the absorption of the radiation over said slice, means for rotating the source and detector means around the body causing said source means to irradiate the slice from a plurality of directions and said detector means to provide further output signals, relating to further substantially linear paths, and processing means arranged to combine some of the output signals provided by the detector means relating to substantially the same path through the body, but obtained at different times in said rotation, in accordance with a predetermined amplitude ratio which varies throughout a predetermined angular range of said rotation.

3. An apparatus according to claim 2 wherein the means for rotating is arranged to rotate the source and detector means through a total angle of substantially $(\pi + \theta)$ where $\theta$ represents the predetermined angular range of said rotation.

4. An apparatus according to claim 3 where $\theta$ is approximately 20°.

5. A medical radiographic apparatus comprising: means for defining a patient position, means for generating a beam of penetrating radiation which travels in a substantially planar region intersecting the patient position, means for orbiting the beam of radiation within said region around an axis located within the patient position, said orbiting means rotating the beam of radiation over an angle exceeding half a revolution, means for detecting the radiation emerging from the patient position in said region along a plurality of radiation beam paths which are at an angle to each other in said region to obtain a corresponding measurement signal for each of said beam paths, means for combining the measurement signals for pairs of beam paths where each pair comprises beam paths along the same line but at opposite directions, said combining means providing a resulting combined measurement signal for each pair, said combined signal being determined by a contribution from the measurement signal for each of the beam paths of the pair corresponding to the angular position of the beam path within said region and means for processing said combined signals and measurement signals for other beam paths to derive a representation of the distribution in said region of a characteristic related to the response to said radiation of the matter traversed by the beam paths.

6. An apparatus for examining a body by means of penetrating radiation such as X- or γ-radiation including source means arranged to irradiate a cross-sectional slice of the body, detector means responsive to said radiation and disposed to receive said radiation after passage through the body along each of a plurality of substantially linear beam paths, and to provide output signals indicative of the amount of said radiation transmitted through said body along each of said beam paths, means for rotating the source and detector means around the body causing said source means to irradiate the body from a plurality of directions and said detector means to provide further output signals indicative of the amounts of said radiation transmitted through said body along further substantially linear beam paths, said rotating means causing paths in respect of which output signals were provided at an initial stage of said rotation to be irradiated again at a later stage of said rotation and means being provided for weighting output signals relating to the radiation transmitted through the body along a given beam path at said different stages of said rotation by respective complementary weighting factors and for combining the singals so weighted to produce composite signals; said weighting factors applied to signals obtained during said initial stage of said rotation gradually increasing in amplitude with increasing angle of said rotation and said weighting factors applied to signals obtained during said further stage of said rotation gradually decreasing in amplitude with increasing angle of said rotation, said increase and decrease in amplitude of said weighting factors being such as to produce said complementary relationship between the weighting factors applied to the output signals relating to a given path.

* * * * *